United States Patent [19]

Schomäcker et al.

[11] Patent Number: 5,583,252
[45] Date of Patent: Dec. 10, 1996

[54] PROCESS FOR PREPARING 4,4'-DINITROSTILBENE-2,2'-DISULPHONIC ACID AND ITS SALTS

[75] Inventors: Reinhard Schomäcker; Helmut Waldmann; Hans-Joachim Traenckner, all of Leverkusen, Germany

[73] Assignee: Bayer Aktiengesellschaft, Leverkusen, Germany

[21] Appl. No.: 444,603

[22] Filed: May 19, 1995

[30] Foreign Application Priority Data

May 26, 1994 [DE] Germany ............... 44 18 305.4

[51] Int. Cl.$^6$ .................................... C07C 309/32
[52] U.S. Cl. ...................................... 562/60
[58] Field of Search ............................... 562/60

[56] References Cited

U.S. PATENT DOCUMENTS

| | | |
|---|---|---|
| 4,680,146 | 7/1987 | Skipa et al. . |
| 4,719,051 | 1/1988 | Guglielmetti . |
| 4,952,725 | 8/1990 | Lund et al. . |
| 5,041,632 | 8/1991 | Guglielmetti . |

FOREIGN PATENT DOCUMENTS

| | | |
|---|---|---|
| 0641773 | 3/1995 | European Pat. Off. . |
| 2136430 | 9/1984 | United Kingdom . |

OTHER PUBLICATIONS

Derwent Abstracts, Week 9521, General Chemistry–p. 3 JP 07082238 (1994).
Chem. Abstr., 41–Dyes, 157977d, vol. 106, 1987, p. 85.
Chem. Abstr., 45–Industrial Organics, 79944y, vol. 112, 1990, p. 147.

Primary Examiner—Nicky Chan
Attorney, Agent, or Firm—Sprung Horn Kramer & Woods

[57] ABSTRACT

The preparation of 4,4'-dinitrostilbene-2,2'-disulphonic acid by oxidation of 4-nitrotoluene-2-sulphonic acid with oxygen in alkaline medium in aqueous ether alcohol makes possible a simplified work-up.

11 Claims, No Drawings

PROCESS FOR PREPARING 4,4'-DINITROSTILBENE-2,2'-DISULPHONIC ACID AND ITS SALTS

The invention relates to a process for preparing 4,4'-dinitrostilbene-2,2'-disulphonic acid (hereinafter: "DNS") and its salts by oxidation of 4-nitrotoluene-2-sulphonic acid (hereinafter: "NTS") with oxygen in an alkaline medium. The process is distinguished by an elegant isolation of the desired product.

DNS is an important intermediate for the preparation of optical brighteners; it is therefore prepared on a large scale.

Processes for preparing DNS by oxidation of NTS with oxygen in aqueous alkaline medium are known (DD 240 200, German Offenlegungsschrift 3 409 171 and 3 519 552, EP-A 305 648). A problem here is the poor solubility of NTS in sodium and potassium hydroxide solutions. If very good yields are obtained at all, these processes use high dilution, long reaction times or are carried out under pressure or they are uneconomical with regard to the wastewater formed and were therefore unsatisfactory.

It has also already been proposed that the reaction be carried out in dipolar aprotic solvents (EP-A 26 154 and 332 137). On the one hand, it is desirable to use NTS as an aqueous solution or in a moist state, i.e. to omit complete drying in the preparation of NTS. On the other hand, our own experiments have shown that the presence of water greatly impairs the yield when working in dipolar aprotic solvents.

It has now been found that the use of an aqueous solution of certain ether alcohols makes possible a favourable reaction procedure with high yield and a greatly simplified work-up.

The invention accordingly provides a process for preparing compounds of the formula

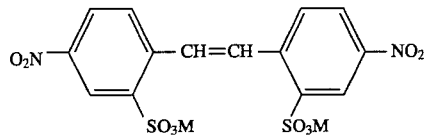

in which M represents hydrogen, sodium or potassium, by oxidation of 4-nitrotoluene-2-sulphonic acid with oxygen in a solvent at temperatures of from 30° to 80° C., preferably from 35° to 55° C.,
characterized in that the solvent used is a mixture of a) from 50 to 70% by weight of water and b) from 30 to 50% by weight of ether alcohol, where the percentages implicated are based on the sum (a+b) and the ether alcohol has the formula $$C_iH_{2i+1}(OCH_2CH_2)_j-OH \quad (II)$$

where i is from 2 to 10, preferably from 2 to 5, and j is from 1 to 6, preferably from 1 to 3.

For the purposes of the present invention, the term "oxygen" also includes mixtures of oxygen with other gases such as carbon dioxide or nitrogen. The most economical form is atmospheric air. It is advantageous to distribute the oxygen in the reaction mixture as finely as possible, for example by use of suitable nozzles.

The reaction is advantageously carried out in the presence of bases. Preferred bases are alkali metal hydroxides, with sodium and potassium hydroxide being particularly preferred. The amount of base can vary within wide limits; it depends, inter alia, on whether the NTS is used as free acid or as salt. When using the NTS as free acid, the base is required in more than the equivalent amount since one equivalent of base is consumed in the neutralization of the sulphonic acid group. The base is preferably used in an amount of from 1.5 to 8, preferably from 2 to 5, equivalents per mol of NTS (free acid).

It can be advantageous to carry out the process of the invention with addition of a catalyst, but this is not absolutely necessary. Catalysts used are, in particular, compounds of the transition metals, for example of Co, Cr, Fe, Ni, Cu, Nb, Ta, Ru, preferably Mn and V. It is possible to use these metals in the form of their salts with inorganic acids, for example the metal fluorides, chlorides, sulphates, nitrates, carbonates, phosphates; the metal oxides and metal hydroxides; the metal salts of organic acids, for example the metal acetate, oxalates, phenoxides, benzoates, salicylates; complexes of these metals, for example with acetylacetone, N,N'-disalicylidene-ethylenediamine, ethylene diamine, diethylenetriamine, triethylenetetramine, tetraphenylporphine and phthalocyanine.

The catalysts can be used in amounts of from 0.1 to 10 g, preferably from 0.2 to 1 g, in each case per kg of reaction mixture.

Preferred etheralcohols comprise the $C_1$–$C_{10}$-alkyl ethers, in particular the methyl, ethyl, propyl, butyl, pentyl and hexyl ethers of ethylene glycol, diethylene glycol, triethylene glycol, tetraethylene glycol, pentaethylene glycol and hexaethylene glycol. Particular preference is given to the ethyl, propyl and butyl ethers of diethylene and triethylene glycol, in particular ethylene glycol monoethyl and monobutyl ethers. In a particularly preferred embodiment, use is made of a mixture of diethylene glycol monoethyl and monobutyl ethers which forms a single phase with the other components of the reaction mixture under the reaction conditions, but forms two phases under the work-up conditions. Thus, the solvent used for the process of the invention can, for example, consist of a) from 50 to 70% by weight of water, b)i) from 10 to 30% by weight of diethylene glycol monobutyl ether and b)ii) diethylene glycol monoethylether, with the amounts a), b)i) and b)ii) adding up to 100% by weight.

The process of the invention can be carried out, for example, by gassing a solution of NTS in a mixture of from 5 to 10% strength by weight sodium hydroxide or potassium hydroxide solution and ether alcohol at from 30° to 80° C., preferably from 35° to 55° C., with oxygen or air, optionally in the presence of a catalyst. It is sometimes advisable to use initially only a fraction of the amount of NTS and to meter in the remainder, optionally as a solution in water or ether alcohol, during the course of the reaction. The progress of the reaction can be monitored, for example, by thin-layer chromatography. After the reaction is complete, neutralization can be carried out by addition of acid, e.g. sulphuric acid. It has been found that, optionally after neutralization—depending on pH, the DNS itself or its salt (preferably the disodium salt) can be crystallized directly from the reaction mixture by cooling to from 5° to 30° C., preferably from 10° to 25° C. the crystallized product can then be separated off from the mother liquor in a manner known per se, e.g. by filtration or centrifugation.

The salt formed during neutralization aids the separation of the reaction mixture into two phases. It has been found that the desired phase separation (of reaction mixture or mother liquor) can be further assisted by setting the temperature to from 60° to 100° C., preferably from 70° to 80°

C. The aqueous phase contains inorganic salts and water-soluble reaction byproducts, the organic phase contains DNS which has not crystallized out and possibly unreacted starting material. The phase separation is further helped by the addition of nonpolar organic solvents. Suitable nonpolar organic solvents for the extraction comprise, for example, aliphatic, cycloaliphatic and aromatic $C_5$–$C_{18}$-hydrocarbons such as n-pentane, iso-pentane, n-hexane, cyclohexane, n-heptane, n-octane, iso-octane, n-nonane, iso-nonane, n-decane, n-undecane, n-dodecane, iso-dodecane, n-tridecane, n-tetradecane, n-pentadecane, n-hexadecane, iso-hexadecane, n-heptadecane, n-octadecane, benzene, $C_1$–$C_9$-alkylbenzenes such as toluene, xylene and mesitylene. The $C_5$–$C_{18}$-hydrocarbons can also be monosubstituted to trisubstituted, preferably monosubstituted, by hydroxyl, chloro, bromo, fluoro, nitro, hydroxy-$C_1$–$C_4$-alkyl or $C_1$–$C_4$-alkoxy. Such solvents include, for example, chlorobenzene, chlorotoluene, 2-ethylhexanol, bis(hydroxymethyl)-cyclohexane and anisole. Particular preference is given to aromatic hydrocarbons; toluene is the most preferred extractant.

According to a preferred embodiment, the phase separation is carried out in the presence of the nonpolar organic solvents at from 60° to 100° C., preferably from 70° to 80° C.

The extractant can be added to the reaction mixture in weight ratios of from 1:0.05 to 1:1. This extraction can be carried out in one or more stages in countercurrent or in crosscurrent in suitable apparatus, such as extraction columns or mixer-settler apparatus. Ether alcohol and valuable materials which do not crystallize can be reextracted from the mother liquor using water and it can be recycled to the reaction; the organic phase of this extraction step predominantly contains the nonpolar organic solvent used for the extraction of the final product, which solvent can be recovered and used without further purification for further extractions.

According to the invention, crystallization and extraction can also be interchanged and the organic valuable materials can be first extracted from the reaction mixture using a nonpolar organic solvent and DNS or its salt can be allowed to crystallize from this extract.

Thus, to work up the extract, the DNS can be crystallized by cooling the extract to from 5° to 30° C., preferably to from 10° to 20° C. The mother liquor is subsequently heated to from 50° to 100° C., preferably from 70° to 80° C., and separates into two phases. To improve the separation, toluene, for example, is added as extractant. The aqueous phase can be extracted with toluene, optionally repeatedly.

The organic phases from the extraction steps can then be combined and cooled to temperatures of from 10° to 20° C. At this temperature, the ether alcohols can be reextracted with water. The amount of water is here preferably selected in such a way that the water/ether alcohol mixture has the composition required for the reaction. The upper phase from this reextraction can be recycled without further purification to the extraction of the mother liquor.

EXAMPLES

Example 1

In a continuously operated apparatus, 1000 g/h of water, 800 g/h of diethylene glycol monoethyl ether, 200 g/h of diethylene glycol monobutyl ether, 145 g/h of NaOH and 200 g/h of NTS were metered into a cascade of four 5 l stirred reactors, of which the first two were maintained at 45° C. and the second two were maintained at 55° C. Each reactor was gassed with 25 l/h of air. The product stream leaving the cascade was neutralized with 180 g/h of conc. sulphuric acid and crystallized at 15°. The mother liquor was admixed with 300 g/h of toluene in a mixer-settler apparatus maintained at 70° C. The separated-off aqueous phase was again extracted with 300 g/h of toluene in a second mixer-settler apparatus maintained at 75° C. The aqueous phase was discarded and the organic phases from the two extractions were combined. By means of extraction with 1000 g/h of water, which was carried out at 15° C., the ether alcohols used and valuable materials which had not crystallized were recovered and, after drawing off residual toluene, were recycled to the reactor cascade. The organic phase, which consists essentially of toluene, was recycled to the extractions of the mother liquor. The yield of this process was >190 g/h of DNS, i.e. >95% of theory.

Example 2

1000 g of water, 800 g of diethylene glycol monoethyl ether, 200 g of diethylene glycol monobutyl ether and 120 g sodium hydroxide were placed in a 2 l stirred reactor and heated to 45° C. After reaching the reaction temperature, the contents of the reactor were gassed with 100 l/h of air. While gassing continually, 100 g of 4-nitrotoluene-2-sulphonic acid were added at the start of the reaction. Over a period of 4 hours, a further 100 g of 4-nitrotoluene-2-sulphonic acid and 25 g of sodium hydroxide were added. After addition was complete, i.e. after 4 hours, the reaction temperature was raised to from 55° to 57° C. and the mixture was allowed to react to completion for 3 hours. To isolate the product, the mixture was, with further oxygen gassing, neutralized with concentrated sulphuric acid. The reaction mixture was then brought to a temperature of 75° C. and admixed with 300 g of toluene. At this temperature, rapid phase separation into an aqueous and an organic phase occurred. The aqueous phase was separated off, again extracted with 300 g of toluene and subsequently discarded. The combined organic phases were crystallized by cooling to from 10° to 15° C. From the mother liquor, product which had not crystallized, diethylene glycol monoethyl ether and diethylene glycol monobutyl ether were extracted at from 10° to 15° C. with water and recycled to the reaction. The yield of 4,4'-dinitrostilbene-2,2'-disulphonic acid was determined from the sum of the amount isolated and the content in the mother liquor determined by HPLC. The yield was >95% of theory.

Example 3

In a continuously operated apparatus, 1000 g/h of water, 800 g/h of diethylene glycol monoethyl ether, 200 g/h of diethylene glycol monobutyl ether, 145 g/h of sodium hydroxide and 200 g/h of NTS were metered into a cascade of four 5 l stirred reactors which was maintained at 50° C. Each reactor was gassed with 25 l of air per hour. The product stream leaving the cascade was, in a mixer-settler apparatus maintained at 70° C., neutralized with 180 g/h of concentrated sulphuric acid and admixed with 300 g/h of toluene. The separated-off aqueous phase was again extracted with 300 g/h of toluene in a second mixer-settler apparatus maintained at 75° C. The aqueous phase was discarded, the organic phases from the two extractions were combined and crystallized at 15° C. From the mother liquor, the ether alcohols used and valuable materials which had not crystallized were recovered by extraction at 15° C. with 1000 g/h of water and, after drawing off residual toluene, were recycled to the reactor cascade. The organic phase, which consists essentially of toluene was recycled to the extractions. The yield of this process was >190 g/h of DNS, i.e. >95% of theory.

We claim:

1. Process for preparing compounds of the formula

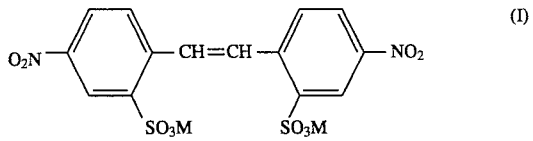

in which M represents hydrogen, sodium or potassium, by oxidation of 4-nitrotoluene-2-sulphonic acid with oxygen in a solvent at temperatures of from 30° to 80° C., characterized in that the solvent used is a mixture of a) from 50 to 70% by weight of water and b) from 30 to 50% by weight of ether alcohol, where the percentages implicated are based on the sum (a+b) and the ether alcohol has the formula $$C_iH_{2i+1}(OCH_2CH_2)_j\text{—}OH \qquad (II)$$

where i is from 2 to 10 and j is from 1 to 6.

2. Process according to claim 1, where i is from 2 to 5 and j is from 1 to 3.

3. Process according to claim 1, where the ether alcohol is diethylene glycol monoethyl ether and/or diethylene glycol monobutyl ether.

4. Process according to claim 1, where the solvent consists of a) from 50 to 70% by weight of water, b)i) from 10 to 30% by weight of ethylene glycol monobutyl ether and b)ii) ethylene glycol monoethyl ether, where the amounts a), b)i) and b)ii) add up to 100% by weight.

5. Process according to claim 1, according to which the 4-nitrostilbenesulphonic acid or its salt is allowed to crystallize out at a temperature of from 5° to 30° C.

6. Process according to claim 1, according to which the temperature during a work-up of the reaction mixture is set to from 60° to 100° C.

7. Process according to claim 1, according to which a nonpolar organic solvent is added during a work-up of the reaction mixture.

8. Process according to claim 1, according to which the temperature during a work-up of the reaction mixture is set to from 60° to 100° C. and extraction with a nonpolar organic solvent is carried out at this temperature.

9. Process according to claim 1, wherein the ether alcohol b) used is recovered and again used in a subsequent reaction.

10. Process according to claim 7, wherein the nonpolar organic solvent used is recovered and again used in a subsequent reaction.

11. Process according to claim 8, wherein the nonpolar organic solvent used is recovered and again used in a subsequent reaction.

* * * * *